United States Patent [19]
Lidman et al.

[11] Patent Number: 5,865,760
[45] Date of Patent: Feb. 2, 1999

[54] SYSTEM FOR DETECTING CHANGES IN BODY POSTURE

[75] Inventors: Johan Lidman, Stockholm; Jonas Andersson, Johanneshov, both of Sweden

[73] Assignee: Pacesetter AB, Solna, Sweden

[21] Appl. No.: 971,709

[22] Filed: Nov. 17, 1997

[30] Foreign Application Priority Data

Nov. 25, 1996 [SE] Sweden .................................. 9604319

[51] Int. Cl.⁶ ................................................. A61N 1/365
[52] U.S. Cl. ............................................ 600/509; 607/19
[58] Field of Search ................................... 600/509, 516, 600/517, 521; 607/4, 5, 6, 9, 17, 19

[56] References Cited

U.S. PATENT DOCUMENTS

| | | |
|---|---|---|
| 4,583,553 | 4/1986 | Shah et al. .............................. 600/517 |
| 5,354,317 | 10/1994 | Alt . |
| 5,370,667 | 12/1994 | Alt . |
| 5,472,453 | 12/1995 | Alt . |
| 5,593,431 | 1/1997 | Sheldon . |

FOREIGN PATENT DOCUMENTS

| | | |
|---|---|---|
| 0 580 128 | 1/1994 | European Pat. Off. . |
| 8-56914 | 3/1996 | Japan . |

Primary Examiner—William E. Kamm
Assistant Examiner—Kennedy J. Schaetzle
Attorney, Agent, or Firm—Hill & Simpson

[57] ABSTRACT

In a system for detecting changes in body posture, electrocardiograms are recorded. The recorded electrocardiograms analyzed are to determine changes in the body posture of a patient from changes in the morphology of the recorded electrocardiograms. The electrocardiogram analysis can be augmented by obtaining and analyzing an accelerometer signal as well.

13 Claims, 5 Drawing Sheets

SYSTEM FOR DETECTING CHANGES IN BODY POSTURE

BACKGROUND OF THE INVENTION

1. Field of the Invention

The present invention relates to a system for detecting changes in body posture.

2. Description of the Prior Art

Most sensors for measuring different physiological parameters of a subject, like pressure, electrical impedance etc., are affected by changes in the body posture of the subject. Thus more accurate and reliable information can be obtained if the body posture is known. In U.S. Pat. No. 5,370,667 a device and a method are described for automatically adjusting tachycardia recognition criteria based on detected physical activity of the patient. In this way it is possible to discriminate between physiological and pathological tachycardias. The activity sensor, which is an accelerometer of a piezoelectric, piezoresistive or piezocapacitive type, determines the activity status of the patient, including the position of the patient, and this information is used to adjust a threshold rate for the tachycardia recognition criterion of an ECG.

Furthermore, the body responds to a change in body posture from supine to standing by a transient increase in the heart rate (see U.S. Pat. No. 5,354,317). In this patent an apparatus and a method for cardiac pacing responsive to patient position are described, the same types of accelerometer as mentioned above being proposed for detecting changes in posture of the patient. This information is used for controlling the pacing rate, in a manner which is as physiologically correct as possible.

It has now been observed that body posture changes result in immediate changes in the morphology of the ECG. Thus FIG. 1 shows average ECGs for a number of cardiac cycles with the patient in the supine position and in a sitting upright position, respectively. As can be seen from this FIG. 1, the two positions of the patient are reflected in a characteristic difference in the surface ECG after the QRS complex. FIGS. 2 and 3 respectively illustrate an average IECG of two patients for a number of cardiac cycles for three different positions, standing, sitting and supine. Also in FIGS. 2 and 3, characteristic changes in the average IECGs can be observed for the different body postures of the patient, these differences being more pronounced in certain portions of the cardiac cycle then in other portions.

SUMMARY OF THE INVENTION

An object of the present invention is to provide a system for detecting body posture changes which is based on the observed changes in surface ECGs as well as in IECGs resulting from changes in the body posture.

This object is achieved, according to the invention in a system for detecting body posture changes having means for recording electrocardiograms and analyzer means for determining changes in the body posture of a patient from changes in the morphology of the recorded electrocardiograms.

In an embodiment of the system according to the invention the analyzer means include averaging means for determining a first average value of a specific portion of electrocardiograms recorded during a predetermined, first number of cardiac cycles, and a second average value of the same specific portion of electrocardiograms recording during a predetermined, second number of subsequent cardiac cycles, and means for detecting changes in the body posture from the relation between these average values. The analyzer means also include means for forming a difference between the first average value and the second average value, and the detecting means include first comparison means for comparing this difference with predetermined threshold values, for determining changes in posture from the relation between this difference and the threshold values. Thus the average value of the specific portion of electrocardiograms from, e.g. the ten latest cardiac cycles, is calculated and compared with the average value of this portion of electrocardiograms from the two next occurring cardiac cycles. If the difference between this two average values exceeds a given threshold this indicates a change in body posture.

According to another embodiment of the system of the invention, the aforementioned specific portion of the electrocardiograms is the T-wave of a cardiac cycle. As appears from the discussion above the ST and T segment of the ECG have superior predictive power of posture changes compared to the QRS-complex. Therefore using the difference between T-segments or T-waves is most appropriate.

According to another embodiment of the system of the invention, the first comparison means determines an increase of the difference above an upper, first threshold value as an indication of changed posture from supine to standing, and determines a decrease of the difference below a lower, second threshold value as an indication of changed posture from standing to supine. A change in posture from supine to standing results in a change, e.g. an elevation, of the T-segment. Consequently, if the T-segment then has increased, the patient has changed posture from supine to standing, and if the T-segment has decreased, the patient has changed posture from standing to supine. The changes in the electrocardiogram for certain body posture changes can be determined in advance for a patient in question, and if the body posture changes detecting system according to the invention is used for controlling a heart stimulator. The control unit of the heart stimulator makes use of the detected changes in the electrocardiograms for given body posture changes, so that the heart stimulator is controlled in the desired manner in response to body posture changes of the patient.

According to another embodiment of the system of the invention, an accelerometer is additionally provided to determine changes in the posture of the patient. Thus by combining accelerometer measurements with the ECG measurements, improved reliability in the detected body posture changes is obtained.

In another embodiment of the system of the invention, an AND-gate is connected to the first and second comparison means to receive, as input signals, output signals from these comparison means indicating posture changes. The AND-gate delivers an output signal representing a specific change in posture only if both its input signals indicate this specific change in posture. Thus an indication of a certain change in body posture is obtained only if both the ECG measurement and the accelerometer measurement indicate the same change in the body posture.

In another embodiment of the system of the invention, a memory is provided to store the latest detected posture change. It will then be known whether the patient is currently standing or supine.

In accordance with the invention a heart stimulator is provided having a body posture changes detecting system as described above, and a control unit connected to the detecting system for controlling the stimulation rate in response to detected posture changes. More precisely, in response to a detected posture change of the patient from supine to standing, the control unit increases the stimulation rate to an increased value exceeding the normal value for a patient in standing position, and then lowers the stimulation rate to the normal value within a predetermined period of time after the increase. By controlling the heart stimulator to produce such a temporary increase in the stimulation rate a physiologically proper increase of the stimulation rate, is produced when the body posture changes from supine to standing.

DESCRIPTION OF THE PREFERRED EMBODIMENTS

Figure 1:
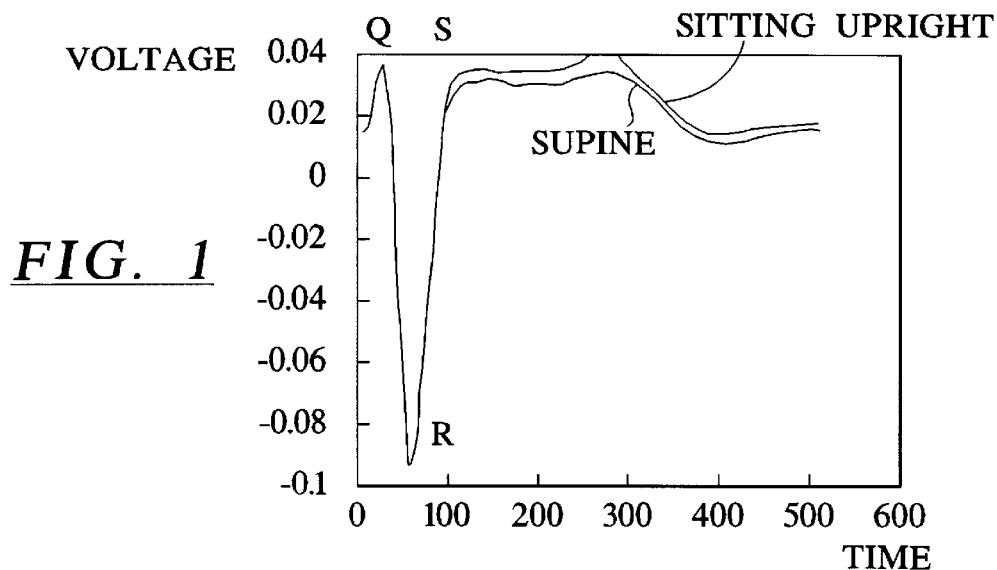
FIGS. 1–3, as noted above, show average values of ECGs recorded for different body postures.
Figure 2:
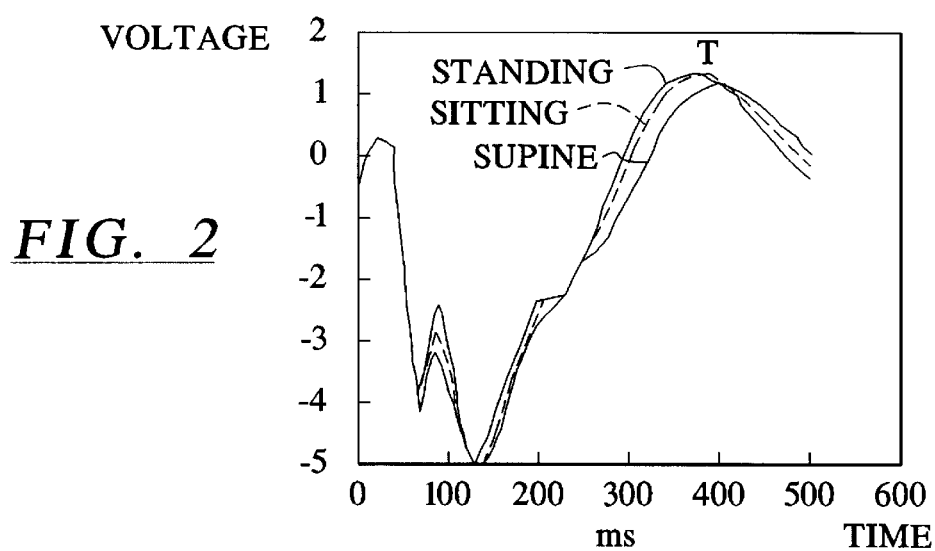
Figure 3:
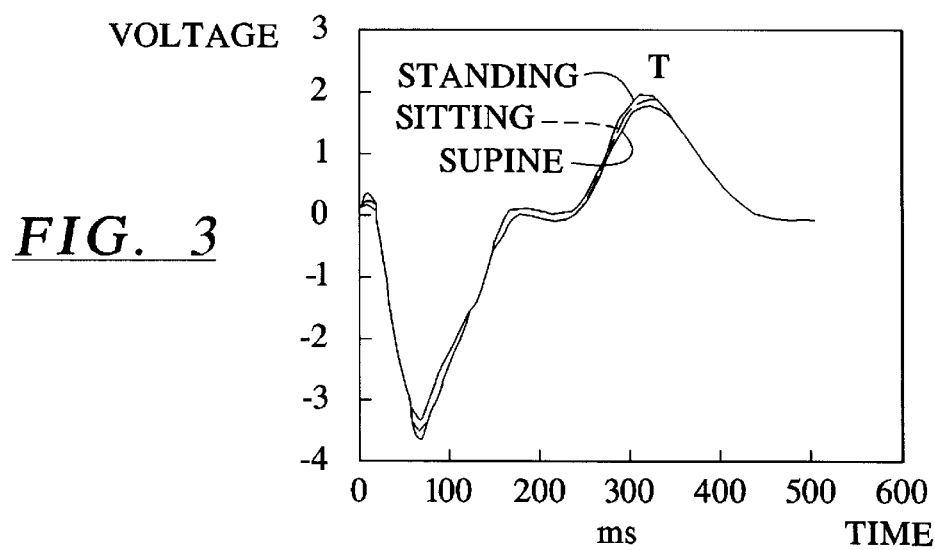

FIGS. 1–3 show, as explained above, surface ECGs and IECGs with the signal intensity shown on an arbitrary voltage scale as a function of time. As discussed above the differences between the ECG signals for different body postures are most pronounced in the ST and T segments of the cardiac cycle and these segments of the ECGs are therefore preferably used for the detecting system according to the invention.

Figure 4:
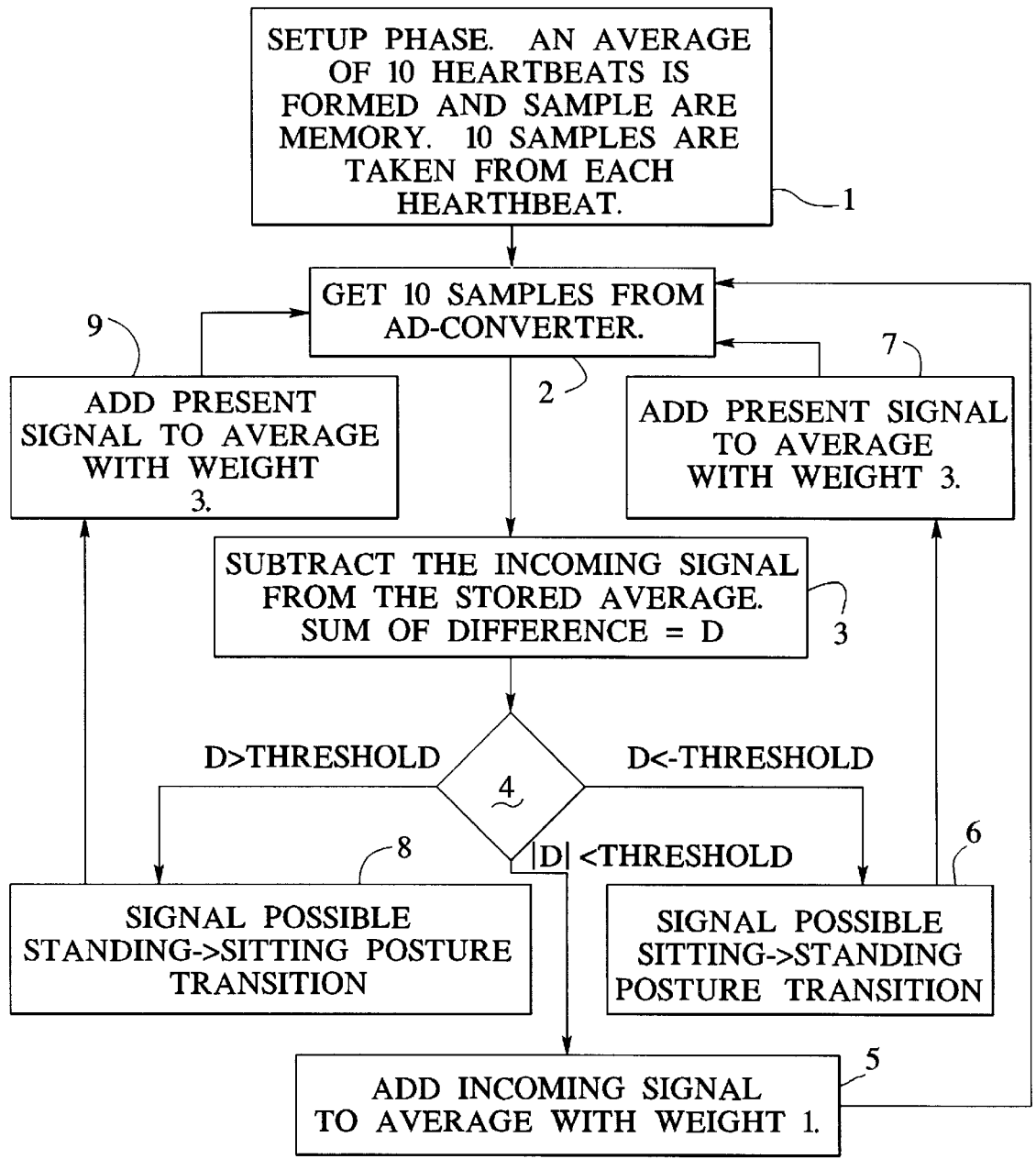
FIG. 4 is a flow diagram for describing the operation of a first embodiment of the detecting system according to the invention.

In FIG. 4 a flow diagram is shown for describing a first embodiment of the detecting system according to the invention in which body posture changes are detected from IECGs.

In the setup phase 1, IECGs are recorded and averaged for 10 heartbeats or cardiac cycles. The sampling of the waveform is triggered by the QRS complex or, where appropriate, by a cardiac stimulation pulse. After an event is triggered the sampling circuit is delayed for roughly 300 ms and then it samples for 100 ms. Approximately 10 samples should be acquired during a cardiac cycle. The samples are taken at a time in the cardiac cycles corresponding to the T-wave. The average value is stored in a memory. It is of course possible, where appropriate, to sample larger portions of an IECG.

In step 2 a new heartbeat is sampled according to the procedure described in connection with step 1.

At step 3 the new values are subtracted from the stored average values at each of the 10 sample points to obtain a difference D for each pair of points (old and new)

In step 4 the sum of the differences D obtained in step 3 is compared to a threshold value and depending on the results of this comparison the operation continuous to step 5, step 6 or step 8. The threshold value has to be established by routine experimentation or may have to be set for each individual. If the absolute value of the difference D is less than the threshold value, the algorithm illustrated in FIG. 4 only updates the average value and cycles back to step 2, at step 5. If the difference D is greater than the threshold value this indicates a posture change, e.g. from standing to sitting position, however, the exact position change or transition indicated may differ from individual to individual. If the difference D is less than the negative threshold value an opposite posture change or transition is indicated, e.g. from sitting to standing position, in step 6.

In step 7 and 9 the running average value is updated. Since a body change or transition has taken place the new value will have greater impact compared to the old values. In the example shown in FIG. 4, the new value is given the weight 3, however, other weights can of course be chosen.

The above described embodiment of the system for detecting body posture changes can include an accelerometer, e.g. a piezoelectric sensor, for determining body posture changes from measured accelerations.

Figure 5:
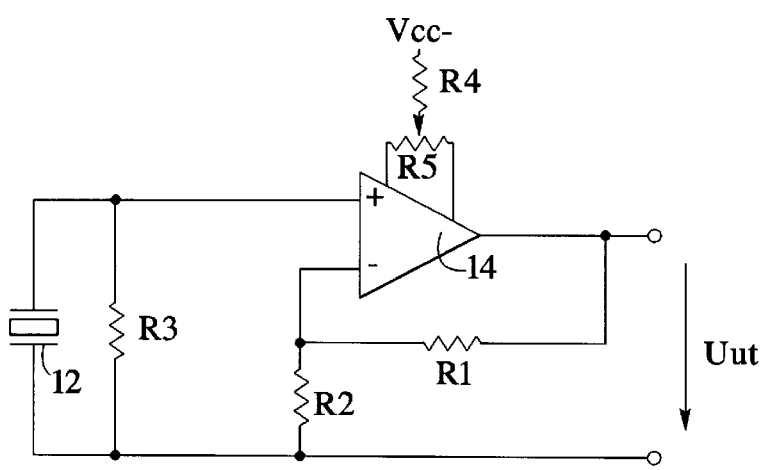
FIG. 5 shows the circuitry of an accelerometer which can be used in the detecting system according to the invention.

FIG. 5 shows a piezoelectric accelerometer 12 connected to an operation amplifier 14. The accelerometer 12 has a capacitance of about 700 pF and, together with the resistor $R_3$, forms a high pass filter with a cut-off frequency of 0.2 Hz for $R_3$=1 Gohm. The high pass filtering DC-components are removed from the signal. The supply voltage $V_{cc}$ can be chosen to be ± 9V and the amplification of the amplifier circuit is $1+R_1/R_2 \approx 100$, for $R_1$=100 kohm and $R_2$=1 kohm. $R_5$ is a trimming potentiometer used for adjusting the offset, when the inputs of the amplifier circuit are open. The components of the amplifier circuit are preferably provided on a printed circuit card and the accelerometer is attached to a cap bracket fixed to the circuit card.

Figure 6:
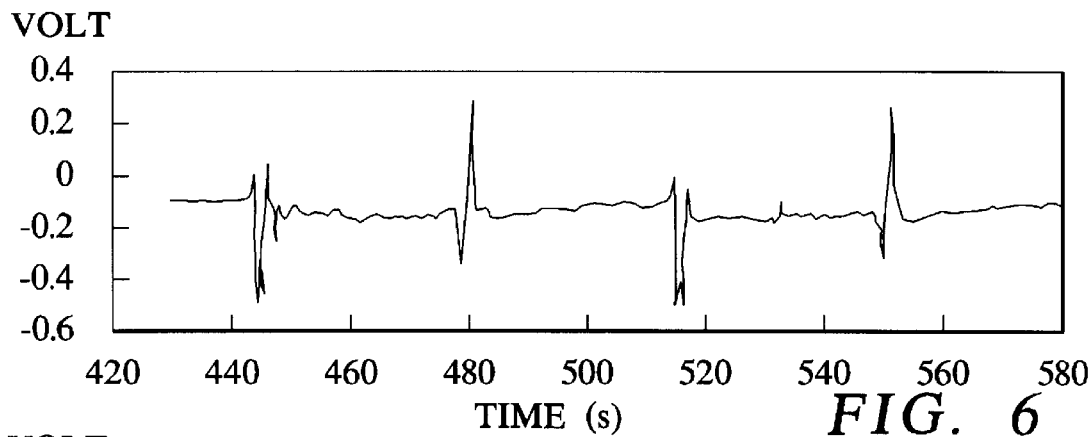
FIGS. 6 and 7 show the obtained accelerometer signal, unfiltered and filtered respectively, when the body posture is changed.
Figure 7:
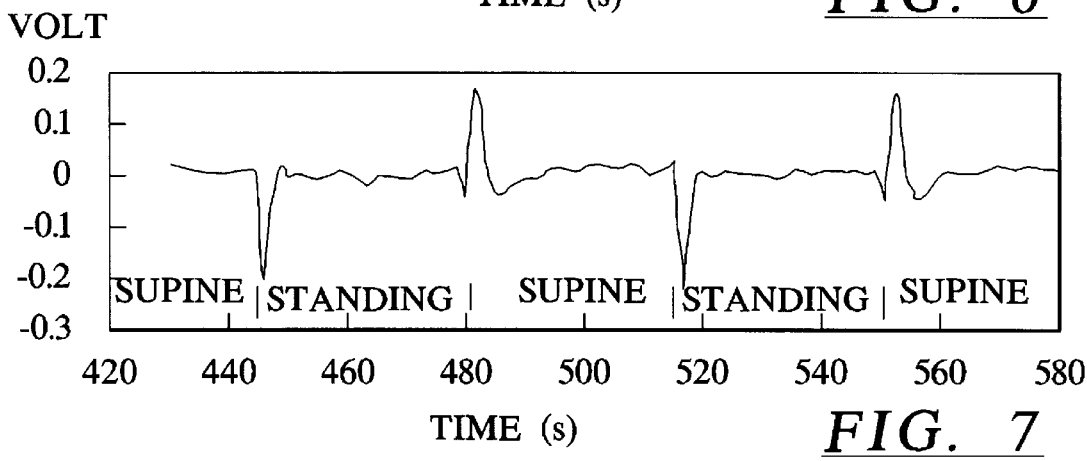

FIGS. 6 and 7 show the signal obtained from a patient who lies down and then stands up, by the accelerometer and amplifier circuit shown in FIG. 5. FIG. 7 shows the signal from FIG. 6 after low pass filtering.

Figure 8:
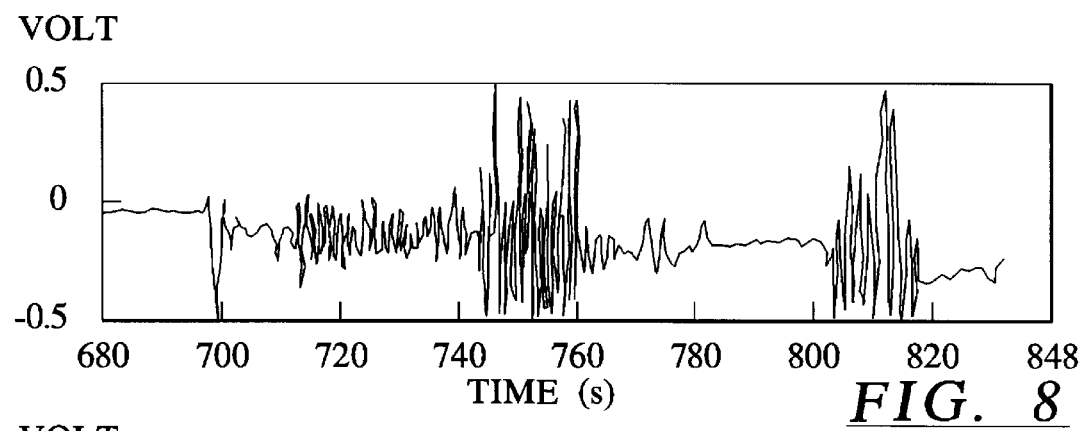
FIGS. 8 and 9 show the accelerometer signal, unfiltered and filtered respectively, when the body posture is changed and for different activities of the patient.
Figure 9:
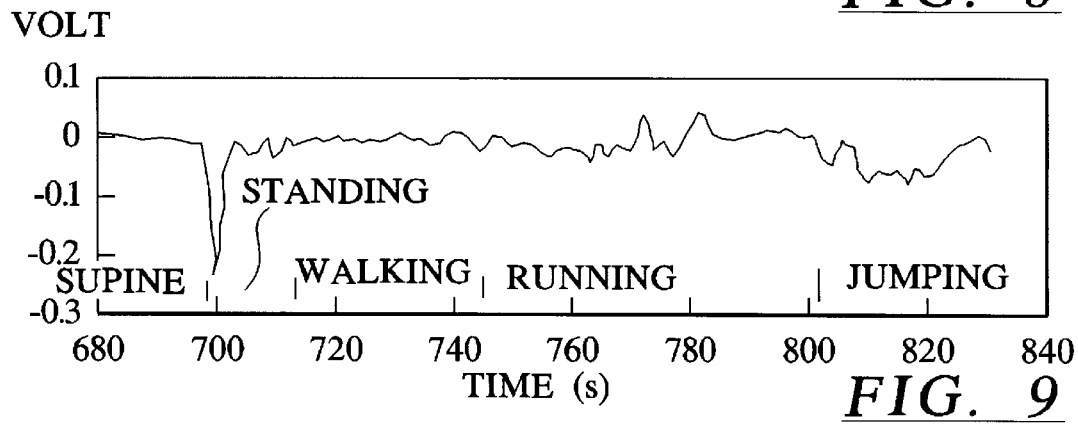

FIG. 8 shows the signal obtained with the accelerometer and the amplifier circuit in FIG. 5 from a patient who is changing position from supine to standing, who is walking in place, running at the place and jumping at the place as indicated in FIG. 9. FIG. 9 shows the signal in FIG. 8 in a filtered version where the offset is reduced. The signal is also low pass filtered with a second order Butterworth filter with a cut-off frequency of 0.2 Hz. FIG. 9 illustrates that the filtering is effective in getting rid of signal contributions from body movements usually used for rate response control, yet the change of body posture can be clearly extracted also from the filtered accelerations.

FIG. 6–9 show the signals in volts as a function of time.

Especially FIGS. 7 and 9 show that the accelerometer signal after suitable processing is well suited for detecting body posture changes. Thus transgression of an upper threshold by the signal can form an indication of a body posture change from standing to supine and transgression of the signal below a lower threshold value can form an indication of a body posture change from supine to standing.

Figure 10:
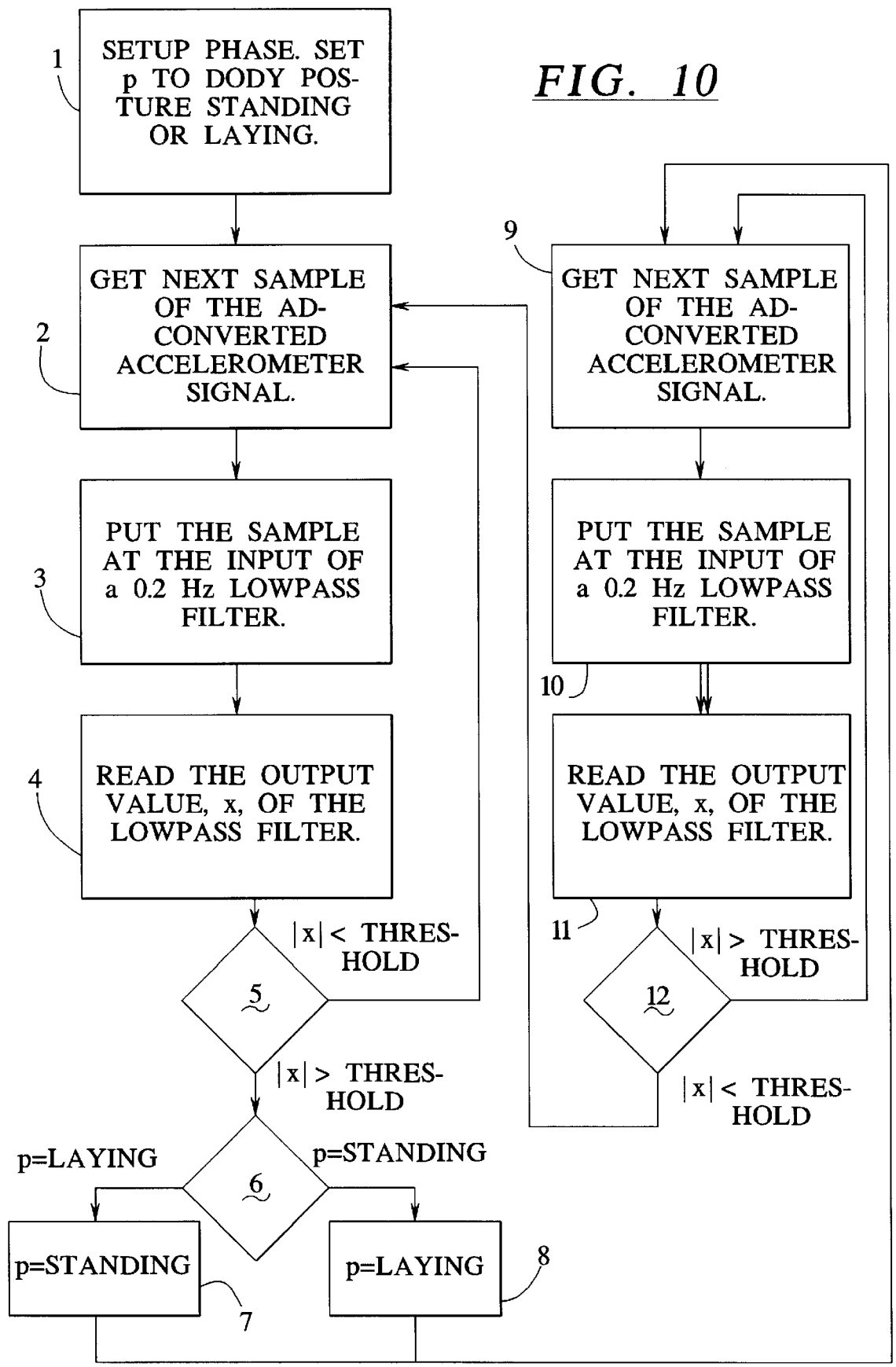
FIG. 10 is a flow diagram for explaining the operation of the accelerometer part of the detecting system according to the invention.

A flow diagram illustrating the determination of body posture by the accelerometer signal is shown in FIG. 10. In step 1, the setup phase, the variable p is set to the body posture standing or laying according to the actual body posture. Steps 2 to 5 wait for a change in body posture.

In step 2 the next sample of the AD-converted accelerometer signal is taken.

In step 3 the signal is low pass filtered with a second order Butterworth filter with a cut-off frequency of 0.2 Hz.

In step 4 the output value x of the low pass filter is read.

In step 5 the absolute value of x is compared with a threshold value to determine whether a change in body posture has occurred. Depending on the result the operation cycles back to step 2 or continues to step 6. If no body posture change is detected the operation is restarted from step 2.

Steps 6 to 8 determine a new body posture as a result of IxI being larger than a threshold value.

If the body posture is supine, (p=supine), the operation continuous from step 6 to step 7. If the existing body posture is standing, (p=standing), the operation continuous from step 6 to step 8.

In step 7 the body posture is changed from supine to standing.

In step 8 the body posture is changed from standing to supine.

Steps 9 to 12 wait until the measured pulse due to changes in body posture has passed or decayed.

In step 9 a new value is sampled from the accelerometer signal.

In step 10 the signal is filtered with a second order Butterworth filter with a cut-off frequency of 0.2 Hz.

In step 11 the output value x of the low pass filter is read.

In step 12 the absolute value of x is compared to a threshold value and if the absolute value of x is less than the threshold value, the operation is cycled back to step 9, otherwise it cycles back to step 2.

Figure 11:
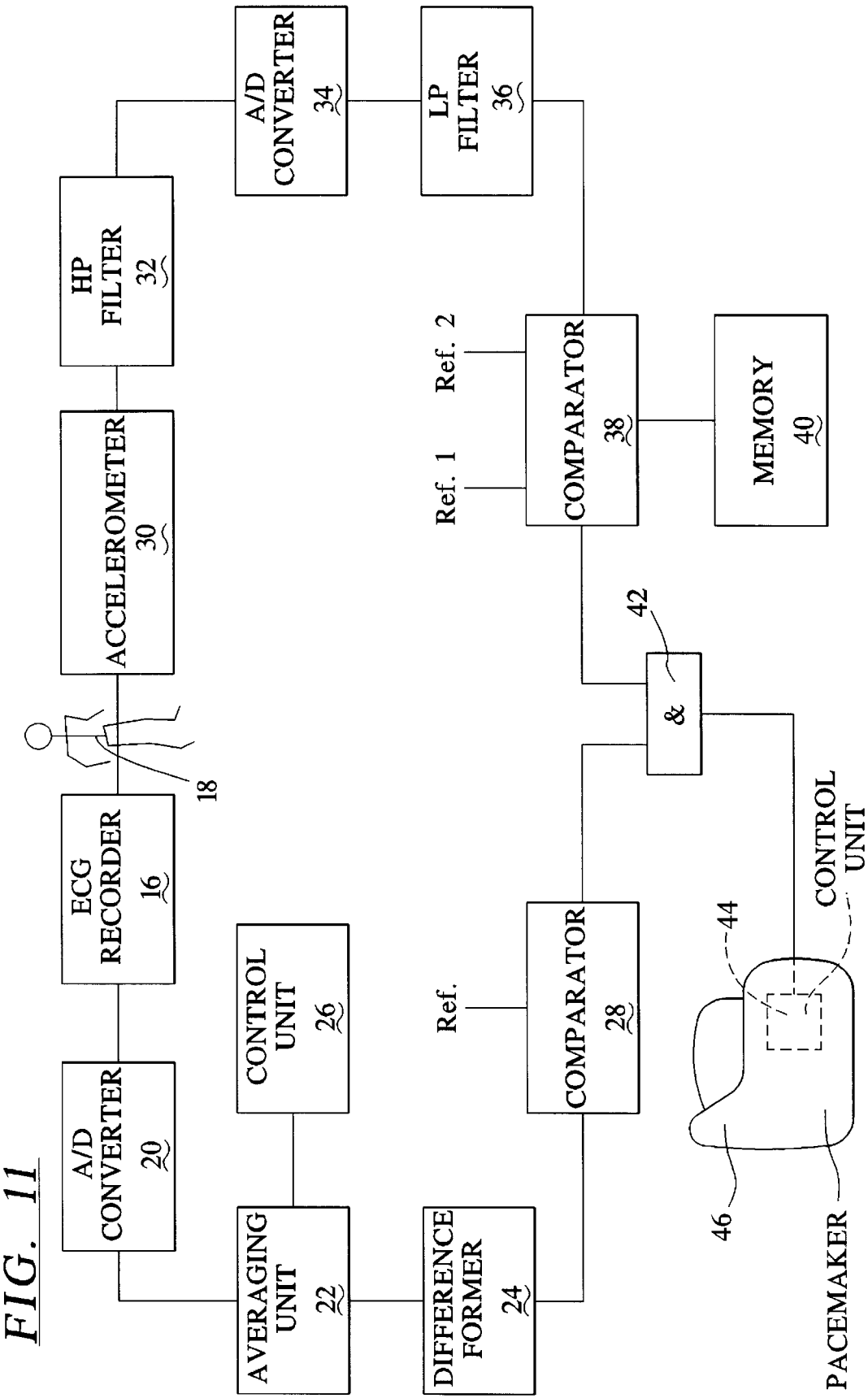
FIG. 11 is a block diagram of an embodiment of the detecting system according to the invention combining recorded ECGs and accelerometer signals for determining body posture changes.

In FIG. 11 a block diagram is shown of an embodiment of the detecting system according to the invention in which the ECG measurements are combined with accelerometer measurements.

An ECG recorder 16 is connected to a patient 18 and the ECG signal is A/D converted in A/D convertor 20. In an averaging unit 22 an average value of the ten latest T-waves or the ten latest ST segments is calculated and is compared with the average value of the two next arriving T-waves or ST segments, in a difference former 24. The operation of the averaging unit 22 is controlled by a control unit 26.

In a comparator 28 the difference between the two above mentioned average values is compared to a threshold or reference value, and if the T-wave or ST segment has increased the patient has changed posture from supine to sitting or standing and if the T-wave or ST segment has decreased the patient has changed posture from standing or sitting to supine, cf. FIGS. 1–3.

An accelerometer 30 is also measuring movements and posture changes of the patient 18. The output signal from the accelerometer 30 is amplified and high pass filtered in a circuit according to FIG. 5, at 32. As a result of the high pass filtering, DC components are filtered out of the signal to get rid of the offset from the amplifier. The signal is then A/D converted and low pass filtered, in units 34 and 36 respectively. The low pass filter 36 is preferably a second order Butterworth filter with a cut-off frequency of 0.2 Hz, and as a result of this low pass filtering frequency components related to other body movements than body posture changes are filtered away, as described above.

In the comparator 38 the low pass filtered signal is compared to threshold or reference values to determine body posture changes of the patient 18. If the signals exceed an upper threshold, Ref 1, this indicates that the body posture changes from standing to supine, and if the signal decreases below a lower threshold, Ref 2, this indicates that the body posture changes from supine to standing, cf. FIGS. 6 and 7. A memory 40 is connected to the comparator 38 to store the last detected posture change. It is then known whether the patient is standing or is in a supine position.

The outputs of the comparators 28 and 38 are connected to the inputs of an AND-gate 42, the output of which is connected to a control unit 44 of a pacemaker 46, such that the stimulation rate of the pacemaker 46 is controlled by detected body posture changes. In this way the pacemaker 46 can be operated as physiologically correctly as possible. Thus if a posture change from supine to standing is detected the stimulation rate is increased for about 5 seconds, whereupon the stimulation rate is gradually lowered to a "normal" rate for a standing patient.

By using an AND combination of the ECG and the accelerometer measurements an improved reliability of the detecting system is obtained. Since body posture changes are detectable by each of the ECG measurements and the accelerometer measurements, however, an OR type combination of the two kinds of measurements could be used as an alternative.

The detecting system according to the invention can also be used for improving the accuracy and reliability of other kinds of measurements. As mentioned in the introduction of this specification a body posture change of a patient gives rise to strong artefacts in e.g. impedance measurements or blood pressure measurements on the patient. By using the body posture changes detecting system according to the invention in connection with such measurements it is possible to eliminate or compensate for such artefacts related to body posture changes.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system for detecting changes in body posture comprising:

means for recording electrocardiograms from a subject, said electrocardiograms exhibiting a changing morphology; and analyzer means, supplied with said electrocardiograms, for determining changes in body posture of said subject from changes in the morphology of said electrocardiograms.

2. A system as claimed in claim 1 wherein said analyzer means comprises:

averaging means for determining a first average value of a predetermined portion of electrocardiograms recorded during a predetermined, first number of cardiac cycles, and for determining a second average value of said predetermined portion of electrocardiograms recorded during a predetermined, second number of subsequent cardiac cycles; and means for identifying a relation between said first average value and said second average value and for identifying changes in body posture dependent on said relation.

3. A system as claimed in claim 2 wherein said means for determining a relation comprises means for forming a difference between said first average value and said second average value, and means for comparing said difference with at least one threshold value for identifying said changes in body posture dependent on a magnitude of said difference relative to said threshold value.

4. A system as claimed in claim 3 wherein said means for comparing comprises means for comparing said difference to an upper, first threshold value and for indicating a change in posture from supine to standing if said difference upwardly transgresses said upper, first threshold value, and for comparing said difference to a lower, second threshold value and for indicating a change in posture from standing to supine if said difference downwardly transgresses said lower, second threshold value.

5. A system as claimed in claim 2 wherein said predetermined portion of said electrocardiograms comprises a T-wave of a cardiac cycle.

6. A system as claimed in claim 1 further comprising an accelerometer which generates an accelerometer signal, and wherein said means for analyzing comprises means for identifying said changes in body posture from a combination of changes in the morphology of the electrocardiograms and said accelerometer signal.

7. A system as claimed in claim 6 wherein said means for analyzing comprises:

processing means for processing said accelerometer signal to obtain a processed signal; and means for comparing said processed signal to at least one predetermined threshold value for generating a posture change-indicating signal, for use in combination with said changes in the morphology of the electrocardiograms, dependent on a relationship of said processed signal to said at least one threshold value.

8. A system as claimed in claim 7 wherein said means for comparing comprises means for comparing said processed signal to an upper, first threshold value and for generating a signal indicating a posture change from supine to standing if said process signal upwardly transgresses said upper, first threshold value, and for comparing said processed signal to a lower, second threshold value and for generating a signal indicating a posture change from standing to supine if said processed signal downwardly transgresses said lower, second threshold value.

9. A system as claimed in claim 6 wherein said accelerometer comprises a sensor selected from the group of sensors comprising piezoelectric electric sensors, piezocapacitive sensors and piezoresistive sensors.

10. A system for detecting body posture changes comprising:

means for recording electrocardiograms from a subject during a predetermined, first number of cardiac cycles and during a subsequent predetermined, second number of cardiac cycles, each electrocardiogram exhibiting a morphology;

averaging means for determining a first average value of a predetermined portion of electrocardiograms recorded during said first number of cardiac cycles, and for determining a second average value of said predetermined portion of electrocardiograms recorded during said second number of cardiac cycles;

means for forming a difference between said first average value and said second average value;

an accelerometer for obtaining an accelerometer signal from said subject;

means for processing said accelerometer signal to obtain a processed signal;

first comparator means for comparing said difference to at least one morphology threshold value to obtain a first comparison result indicating a posture change of said subject;

second comparator means for comparing said processed signal to at least one accelerometer threshold value to obtain a second comparison result indicating a posture change of said subject; and means for combining said first and second comparison results for generating a signal indicating a posture change of said subject dependent on said first and second comparison results.

11. A system as claimed in claim 10 wherein said means for combining comprises an AND gate which generates said signal indicating a posture change of said subject only if said first comparison result is identical to said second comparison result.

12. A system as claimed in claim 10 wherein said first comparator means comprises means for comparing said difference to an upper morphology threshold value and for generating a signal as said first comparison result indicating a posture change from supine to standing if said difference upwardly transgresses said upper morphology threshold value, and for comparing said difference to a lower morphology threshold value and for generating a signal as said first comparison result indicating a posture change from standing to supine if said difference downwardly transgresses said lower morphology threshold value.

13. A system as claimed in claim 10 wherein said second comparator means comprises means for comparing said processed signal to an upper accelerometer threshold value and for generating a signal as said second comparison result indicating a posture change from supine to standing if said processed signal upwardly transgresses said upper accelerometer threshold value, and for comparing said processed signal to a lower accelerometer threshold value and for generating a signal as said second comparison result indicating a posture change from standing to supine if said processed signal downwardly transgresses said lower accelerometer threshold value.

* * * * *